(12) United States Patent
Chapman et al.

(10) Patent No.: US 8,778,646 B1
(45) Date of Patent: *Jul. 15, 2014

(54) METHOD FOR TREATMENT OF MICROORGANISMS DURING PROPAGATION, CONDITIONING AND FERMENTATION USING HOPS ACID EXTRACTS AND ORGANIC ACID

(71) Applicant: Hercules Incorporated, Wilmington, DE (US)

(72) Inventors: John S. Chapman, Lincoln University, PA (US); Corinne E. Consalo, New Castle, DE (US)

(73) Assignee: Hercules Incorporated, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/833,522

(22) Filed: Mar. 15, 2013

(51) Int. Cl.
*C12P 7/10* (2006.01)
(52) U.S. Cl.
CPC ........................................ *C12P 7/10* (2013.01)
USPC .......................................................... 435/165

(58) Field of Classification Search
None
See application file for complete search history.

(56) References Cited

U.S. PATENT DOCUMENTS

| | | |
|---|---|---|
| 6,475,537 B1 | 11/2002 | King et al. |
| 6,620,446 B2 | 9/2003 | King et al. |
| 2004/0044087 A1 | 3/2004 | Maye |
| 2006/0263484 A1 | 11/2006 | Maye |
| 2007/0036882 A1 | 2/2007 | Maye |
| 2008/0206215 A1 | 8/2008 | Ziegler |

FOREIGN PATENT DOCUMENTS

| | | |
|---|---|---|
| WO | 2010111639 | 9/2010 |
| WO | 2011038317 | 3/2011 |

*Primary Examiner* — Suzanne M Noakes
(74) *Attorney, Agent, or Firm* — Joanne Rossi; Michael Herman

(57) ABSTRACT

A method of reducing undesirable microorganism concentration, the method comprises (a) introducing a quantity of fermentable carbohydrate, sugar or cellulose to an aqueous system, (b) introducing a quantity of desirable microorganism to the aqueous system, (c) introducing a hops acid extract into the aqueous system and (d) introducing an organic acid solution into said system.

17 Claims, 1 Drawing Sheet

METHOD FOR TREATMENT OF MICROORGANISMS DURING PROPAGATION, CONDITIONING AND FERMENTATION USING HOPS ACID EXTRACTS AND ORGANIC ACID

FIELD OF THE INVENTION

The present technology relates generally to microbial control in fermentation processes. In particular, the present technology involves a method of reducing or controlling the concentration of undesirable microorganisms.

BACKGROUND OF THE INVENTION

Microorganisms, such as yeast, fungi and bacteria, are used to produce a number of fermentation products, such as industrial grade ethanol, distilled spirits, beer, wine, pharmaceuticals and nutraceuticals (foodstuff that provides health benefits, such as fortified foods and dietary supplements), baking industry and industrial chemicals.

Yeast is commonly used in fermentation processes. One common type of yeast is *Saccharomyces cerevisiae*, the species predominantly used in baking and fermentation. Non-*Saccharomyces* yeasts, also known as non-conventional yeasts, are also used to make a number of commercial products.

Other microorganisms can also be useful in making fermentation products. For example, cellulosic ethanol production, production of ethanol from cellulosic biomass, utilizes fungi and bacteria. Examples of these cellulolytic fungi include *Trichoderma reesei* and *Tichoderma viride*. One example of a bacteria used in cellulosic ethanol production is *Clostridium Ijungdahlii*.

Most of the yeast used in distilleries and fuel ethanol plants are purchased from manufacturers of specialty yeasts. The yeast is manufactured through a propagation process. Propagation involves growing a large quantity of yeast from a small lab culture of yeast. During propagation, the yeast are provided with the oxygen, nitrogen, sugars, proteins, lipids and ions that are necessary or desirable for optimal growth through aerobic respiration.

Once at the distillery, the yeast can undergo conditioning. Conditioning is unlike propagation in that it does not involve growing a large quantity from a small lab culture. During conditioning, conditions are provided to re-hydrate the yeast, bring them out of hibernation and allow for maximum growth and reproduction. The objective of both propagation and conditioning is to deliver a large volume of yeast to the fermentation tank with high viability, high budding and a low level of infection by other microorganisms.

Following propagation and/or conditioning, the yeast enters the fermentation process. The yeast is combined in an aqueous solution with fermentable sugars. The yeast consumes the sugars, converting them into aliphatic alcohols, such as ethanol.

The fermentation process begins with the preparation of a fermentable carbohydrate. In ethanol production, corn is one possible source of fermentable carbohydrate. Other carbohydrate sources including cereal grains and cellulose-starch bearing materials, such as wheat or milo, could also be substituted. Cellulosic biomass such as straw and cornstalks could also be used. Cellulosic ethanol production has recently received attention because it uses readily available nonfood biomass to form a valuable fuel.

The propagation, conditioning and fermentation processes can be carried out using batch or continuous methods. The batch process is used for small-scale production. Each batch is completed before a new one begins. The continuous fermentation method is used for large-scale production because it produces a continuous supply without restarting every time. The hops acid and organic acid blend can be used with either batch or continuous methods.

During the propagation, conditioning or fermentation process the mash or the fermentation mixture can become contaminated with other microorganisms, such as spoilage bacteria. These microorganisms compete with the desired species of yeast for fermentable sugars and retard the desired bio-chemical reaction resulting in a lower product yield. They can also produce unwanted chemical by-products, which can cause spoilage of entire fermentation batches.

Producers of ethanol attempt to increase the amount of ethanol produced from one bushel of cereal grains (approximately 56 pounds (25.4 kilograms)). Contamination by microorganisms lowers the efficiency of yeast making it difficult to attain or exceed the desired levels of 2.8-2.9 gallons of ethanol per bushel (0.42-0.44 liters per kilogram). Reducing the concentration of microorganisms will encourage yeast propagation and/or conditioning and increase yeast efficiency making it possible to attain and exceed these desired levels.

During any of these three processes the yeast can become contaminated with undesirable yeast, bacteria or other undesirable microorganisms. This can occur in one of the many vessels used in propagation, conditioning or fermentation. This includes, but is not limited to, propagation tanks, conditioning tanks, starter tanks, fermentations tanks and piping and heat exchangers between these units.

Bacterial or microbial contamination reduces the fermentation product yield in three main ways. First, the sugars that could be available for yeast to produce alcohol are consumed by the bacteria or other undesirable microorganisms and diverted from alcohol production, reducing yield. Second, the end products of bacterial metabolism, such as lactic acid and acetic acid, inhibit yeast growth and yeast fermentation/respiration, which results in less efficient yeast production. Finally, the bacteria or other undesirable microorganisms compete with the yeast for nutrients other than sugar.

After the fermentation system or vessel has become contaminated with bacteria or other undesirable microorganisms, those bacteria or other microorganisms can grow much more rapidly than the desired yeast. The bacteria or other microorganisms compete with the yeast for fermentable sugars and retard the desired bio-chemical reaction resulting in a lower product yield. Bacteria also produce unwanted chemical by-products, which can cause spoilage of entire fermentation batches. Removing these bacteria or other undesirable microorganisms allows the desired yeast to thrive, which results in higher efficiency of production.

As little as a one percent decrease in ethanol yield is highly significant to the fuel ethanol industry. In larger facilities, such a decrease in efficiency will reduce income from 1 million to 3 million dollars per year.

Some methods of reducing bacteria or other undesirable microorganisms during propagation, conditioning and fermentation take advantage of the higher temperature and pH tolerance of yeast over other microorganisms. This is done by applying heat to or lowering the pH of the yeast solution. However, these processes are not entirely effective in retarding bacterial growth. Furthermore, the desirable yeast microorganisms, while surviving, are stressed and not as vigorous or healthy. Thus, the yeasts do not perform as well.

The predominant trend in the ethanol industry is to reduce the pH of the mash (feed stock) to less than 4.5 at the start of fermentation. Lowering the pH of the mash reduces the population of some species of bacteria. However it is much less effective in reducing problematic bacteria, such as lactic-acid producing bacteria. It also significantly reduces ethanol yield by stressing the yeast used for ethanol production.

Another approach involves washing the yeast with phosphoric acid. This method does not effectively kill bacteria and other microorganisms. It can also stress the yeast used for ethanol production, thereby lowering their efficiency.

Yet another method is to use heat or harsh chemicals to sterilize process equipment between batches. It is ineffective at killing bacteria and other microorganisms within the yeast mixture during production.

In yet another method, antibiotics are added to yeast propagation, conditioning or fermentation batch to neutralize bacteria. Fermentation industries typically apply antibiotics to conditioning, propagation and fermentation processes. Antibiotic dosage rates range between 0.1 to 3.0 mg/L and generally do not exceed 6 mg/L. However, problems exist with using antibiotics in conditioning, propagation and fermentation. Antibiotics are expensive and can add greatly to the costs of large-scale production. Moreover, antibiotics are not effective against all strains of bacteria, such as antibiotic-resistant strains of bacteria. Overuse of antibiotics can lead to the creation of additional variants of antibiotic-resistant strains of bacteria.

Antibiotic residues and establishment of antibiotic-resistant strains is a global issue. These concerns may lead to future regulatory action against the use of antibiotics. One area of concern is distillers grains that are used for animal feed. Distillers grain is the grain residue of the fermentation process. European countries do not allow the byproducts of an ethanol plant to be sold as animal feed if antibiotics are used in the facility. Distiller grain sales account for up to 20% of an ethanol plant earnings. Antibiotic concentration in the byproduct can range from 1-3% by weight, thus negating this important source of income.

In addition, there are other issues to consider when using antibiotics. Mixtures of antibiotics should be frequently balanced and changed in order to avoid single uses that will lead to antibiotic-resistant strains. Sometimes the effective amount of antibiotic cannot be added to the fermentation mixture. For example, utilizing over 2 mg/L of Virginiamycin will suppress fermentation but over 25 mg/L is required to inhibit grown of *Weisella confusa*, an emerging problematic bacteria strain. Overdosing or overuse of antibiotic can stress yeast and impact efficiency or cause regulatory non-compliance.

Industries that employ fermentation for beverages have historically applied hops acid to propagation and fermentation to control unwanted microbes that compete with the yeast for nutrients. With the recent expansion of fuel ethanol, hops acids have been utilized to a minor degree to address unwanted microbes. Competition between yeasts and unwanted microbes results in yield loss of fuel ethanol as unwanted microbes, primarily *Lactobacillus* and *Acetobacter*, reduce the efficiency of fermentation. In beverage production, competing microbes not only reduce efficiency but can alter the aesthetics and taste of the final product.

Organic acids have many applications, including being used as acidifiers, buffers, antioxidants, chelators, synergists, dietary supplements, flavoring agents, preservatives and antimicrobials. Organic acids have been used as preservatives because of their effect on bacteria. The mode of action of organic acid is that the non-dissociated acids penetrate the bacterial cell wall via passive diffusion and disrupt the normal physiology of the cell in two ways: The acids dissociate and therefore lower the internal pH, which is normally close to neutral, impairing the function of the bacteria. The anionic part of the acid that is unable to leave the cell in its dissociated form accumulates within, disrupting metabolic functions and increasing osmotic pressure.

Since small decreases in ethanol yield are highly significant to the fuel ethanol industry, ethanol producers are constantly looking for ways to increase efficiency. Antimicrobials are used to eliminate, reduce or otherwise control the number of microbes in the aqueous systems. However, the use of antimicrobials will always add cost to operations and products and thus more effective ways to achieve microbial control are sought. In addition, some antimicrobials may have deficiencies in either their spectrum of antimicrobial action or operational limitations in their manner of application, such as lack of temperature stability or susceptibility to inactivation by environmental or chemical factors.

DESCRIPTION OF THE INVENTION

Figure 1:
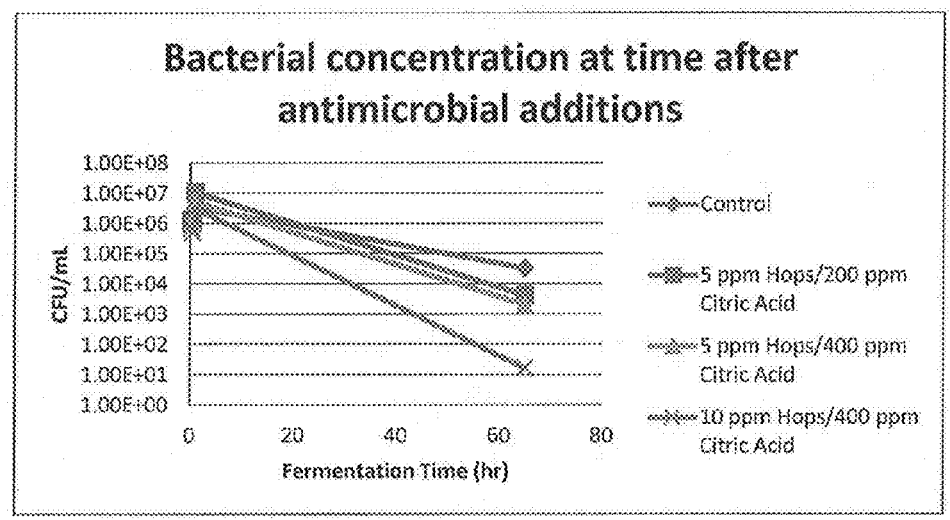
FIG. 1 is graph depicting the bacterial concentrations at time points after antimicrobial addition and at the end of fermentation (64 hours).

In the combination of an organic acid and hops acids in conditioning, propagation and fermentation, it was determined that not only are hops acids compatible with organic acid, but are synergistic when applying both technologies simultaneously. The combination of these products provides a powerful, non antibiotic, antimicrobial treatment. The invention can be used for reducing undesirable microorganism concentration, promoting desirable microorganism propagation, and increasing desirable microorganism efficiency in an aqueous system.

As used herein ppm is measured as mass per volume or 1 ppm equals 1 mg (active) per liter.

As used herein the term "organic acid" is also referring to its salt.

The terms "hops acid" and "hops acid extract" are used interchangeable.

In one aspect of the invention, a method of controlling undesirable microorganism concentration in an aqueous system employed in a fermentation process is disclosed. The method comprising the steps of:
  (a) introducing a fermentable carbohydrate to an aqueous system;
  (b) introducing at least one yeast to said system;
  (c) introducing a hops acid extract into said system; and
  (d) introducing an organic acid into said system.

In one aspect of the invention, a method of controlling undesirable microorganism concentration in an aqueous fluid solution employed in a fermentation process is disclosed. The method comprising the steps of:
  (a) introducing a fermentable carbohydrate to an aqueous system;
  (b) introducing at least one desirable microorganism which is capable of fermenting carbohydrate to said aqueous system;
  (c) introducing at least one hops acid extract into said aqueous system; and
  d) introducing at least one organic acid into said aqueous system.

One non-limiting embodiment of the current method for reducing undesirable microorganism concentration, promoting desirable microorganism propagation, and increasing desirable microorganism efficiency in an aqueous system comprises (a) introducing a fermentable carbohydrate to an aqueous system, (b) introducing at least one yeast or desirable microorganism to the aqueous system, and (c) contacting hops acid extract and organic acid with the fermentable carbohydrate and or yeast.

These steps of the invention can be performed sequentially or in a different order. The hops acids and organic acid can be brought into contact with the yeast or with the fermentation carbohydrate or the yeast and the fermentable carbohydrate can be combined and then the hops acid and organic acid be introduced into the combination of yeast and carbohydrate. The hops acid extract and the organic acid can be blended together and then added to the aqueous system or they can be added separately to the aqueous system. The aqueous system can be in a continuous process or may be a tank in the case of a batch process.

Another non-limiting embodiment of the current method for reducing undesirable microorganism concentration, promoting yeast propagation, and increasing yeast efficiency in an aqueous system comprises (a) introducing a quantity of fermentable carbohydrate to an aqueous system, (b) introducing a quantity of yeast to the aqueous system, and (c) contacting hops acid extract and organic acid with the fermentable carbohydrate and or yeast These steps can be performed sequentially or in a different order. The hops acid extract and the organic acid can be blended together and then added to the aqueous system or they can be added separately to the aqueous system.

In the foregoing method, the "undesirable" microorganisms intended to be reduced are those that compete for nutrients with the desirable microorganisms that promote the desired fermentation processes. Unwanted or undesirable microbes in fermentation include the lactic acid producing bacteria (LAB) and the acetic acid producing bacteria of which *Lactobacillus* and *Acetobacter* are prominent representatives. Any microbe that competes for the fermentable substrate, denying it to the intended fermenting organism and thus reducing yields can be considered undesirable. In this regard, the hops acid extract and organic acid employed in the present method do not detrimentally affect the growth and viability of desirable, fermentation-promoting microorganisms, but does eliminate or suppress the growth of undesirable microorganisms that interfere with the fermentation process. Moreover, the elimination or suppression of undesirable microorganisms has a favorable effect on the growth and viability of desirable microorganisms.

The pH of the aqueous system to be treated is generally is from 3 to 11, or from 3 to 7, or from 4 to 9, or from 4 to 8, or from 4 to 6.5, or from 4.5 to 6. In general, the organic acids work best in systems where the pH of the system is less than least one of the pKa values of the acid or its salt.

Suitable, non-limiting examples of organic acids useful in the present invention include but are not limited to citric acid, benzoic acid, propionic acid, tartaric acid, acetic acid, benzenesulfonic acid, oxalic acid, malic acid, salicylic acid, lactic acid gluconic acid, hydroxyacetic acid and their salts. For purposes of this invention the organic acid is not a hops acid.

Non-limiting examples of hops acids that can be used in the invention include beta acid compounds, alpha acids, isomerized alpha acids, rho isomerized alpha acids, tetra isomerized alpha acids, hexa isomerized alpha acids and hop leaf. Hops acid extract dosages of at least 0.5 ppm and less than 15 ppm or between 2 and 15 ppm or between 5 and 15 ppm or between 5 and 10 ppm can be used in the invention.

In some non-limiting embodiments, the synergistic solution is comprised of hops acid extracts and citric acid or its salt in ratios of 1:10 to 1:6500, or 1:25 to 1:6400, or 1:25 to 1:1600, or from 1:25 to 1:500 or from 1:25 to 1:100

In some non-limiting embodiments, the synergistic solution is comprised of hops acid extracts and propionic acid or its salt in ratios of 1:12.5 to 1:800, preferably 1:12.5 to 1:400, preferably from 1:12.5 to 1:50 or 1:10 to 1:6500, or 1:25 to 1:6400, or 1:25 to 1:1600, or from 1:25 to 1:500.

In some non-limiting embodiments, the synergistic solution is comprised of hops acid extracts and benzoic acid or its salt in ratios of 1:50 to 1:400, preferably 1:50 to 1:200.

The hops acids and the organic acids can be added in single or multiple locations in the fermentation process, including the slurry tank(s), cookers, mash coolers, propagators and fermentation tanks. One skilled in the art may also determine other addition points. The hops acids and the organic acids can be added to a process vessel such as a heatable conditioning tank, capable of performing liquefaction or a yeast propagation vessel. The process vessel could also be a fermentation tank.

In the present method, the concentrations of bacteria and other undesirable microorganisms are reduced while propagation and/or conditioning of desirable microorganisms are encouraged.

It has been discovered that hops acid extracts in combination with at least one organic acid is effective at reducing the concentration of bacteria and other undesirable microorganisms while simultaneously encouraging propagation and/or conditioning of desirable microorganisms. The combination of these products provides a synergistic, antimicrobial treatment without the use of antibiotics.

It has been found that adding a small amount of hops acid extract, for example about 2 to 15 ppm (as measured in the system being treated) or from 5-10 ppm, in conjunction with at least one organic acid results in a synergistic effect. In some non limiting embodiments hops acids are added simultaneously with the organic acid. In other embodiments the hops acid is added separately from the organic acid to the system being treated. The addition of hops acid extracts in conjunction with the addition of organic acids results in improved antimicrobial efficacy.

The production of fuel ethanol by yeast fermentation is used as an example. However, this is merely one illustration. Other fermentation products which could employ the combination of hops acids and organic acids could include distilled spirits, beer, wine, pharmaceuticals, pharmaceutical intermediates, baking products, nutraceuticals (foodstuff that provides health benefits, such as fortified foods and dietary supplements), nutraceutical intermediates, industrial chemical feedstocks, and enzymes. The current method could also be utilized to treat yeast used in the baking industry.

*Saccharomyces* yeasts are one type of useful yeast such as *Saccharomyces cerevisiae*. Non-*Saccharomyces* yeasts can also be used in the invention. Yeast is not the only microorganism used in fermentation. Additional desirable fermenting microorganisms could also be used and benefited by the invention such as the fungi and bacteria typically used in cellulosic ethanol production. Some non-limiting examples of desirable fermenting microorganisms include, but are not limited to, *Trichoderma reesei, Trichoderma viride*, and *Clostridium Ijungdahli.*

Hops acid extracts are useful for killing bacteria, while allowing yeast or other desirable producing microorganisms to survive and thrive. Fermentation industries typically apply hops acid extracts to propagation and fermentation.

The hops acid and organic acid can be added at various points in the propagation, conditioning and/or fermentation processes. The hops acid and the organic acid can be added to cook vessels, fermentation tanks, propagation tanks, conditioning tanks, starter tanks or during liquefaction. The hops acid and organic acid can also be added directly to the corn mash. The hops acid and the organic acid can also be added to the interstage heat exchange system or heat exchangers. The hops acid and organic acid can also be added to the piping between these units or heat exchangers.

The hops acid and organic acid can be added directly into the fermentation mixture. This can be done by adding the hops acid and organic acid in conjunction with the yeast or other desirable microorganism and fermentable carbohydrate, for example during the SSF (Simultaneous saccharification and fermentation) stage.

In a non limiting embodiment the hops acid extract dosages of at least 0.5 ppm and less than 15 ppm is utilized, or a dosage of from 2 and 15 ppm or a dosage of from 3 and 10 ppm or a dosage of from 5 and 10 ppm and organic acid dosages of between 200 and 1000 ppm or greater can be added directly into the fermentation mixture.

The hops acid and organic acid can also be added to the mash prior to the fermentation process. Hops acid extract dosages of at least 0.5 ppm and less than 15 ppm or between 2 and 15 ppm or between 5 and 15 ppm or between 5 and 10 ppm and organic acid dosages of between 200 and 1000 ppm or greater can be added to the mash prior to fermentation.

Hops acid and organic acid can also be added during propagation and/or conditioning. For example hops acid extracts can be added to the yeast slurry replacing an acid washing step.

Hops acid in conjunction with organic acid can be used to achieve improved results in the production of cellulosic ethanol. Cellulosic ethanol is a type of ethanol that is produced from cellulose, as opposed to the sugars and starches used in producing carbohydrate based ethanol. Cellulose is present in non-traditional biomass sources such as switch grass, corn stover and forestry. This type of ethanol production is particularly attractive because of the large availability of cellulose sources. Cellulosic ethanol, by the very nature of the raw material, introduces higher levels of contaminants and competing microorganism into the fermentation process. Hops acid used in conjunction with organic acid can be used in cellulosic ethanol production to control undesirable microorganisms.

There are two primary processes of producing alcohol from cellulose. One process is a hydrolysis process that utilizes fungi, as for example *Trichoderma reesei* and/or *Trichoderma viride*. The other is a gasification process using a bacteria such as *Clostridium Ijungdahlii*. Hops acid in conjunction with organic acid can be utilized in either process.

In the hydrolysis process the cellulose chains are broken down into five carbon and six carbon sugars before the fermentation process. This is either done chemically or enzymatically.

In the chemical hydrolysis method the cellulose can be treated with dilute acid at high temperature and pressure or concentrated acid at lower temperature and atmospheric pressure. In the chemical hydrolysis process the cellulose reacts with the acid and water to form individual sugar molecules. These sugar molecules are then neutralized and yeast fermentation is used to produce ethanol. Hops acid in conjunction with organic acid can be used during the yeast fermentation portion of this method.

Enzymatic hydrolysis can be carried out using two methods. The first is known as direct microbial conversion (DMC). This method uses a single microorganism to convert the cellulosic biomass to ethanol. The ethanol and required enzymes are produced by the same microorganism. Hops acid in conjunction with organic acids can be used during the propagation/conditioning or fermentation steps with this specialized organism.

The second method is known as the enzymatic hydrolysis method. In this method cellulose chains are broken down using cellulase enzymes. These enzymes are typically present in the stomachs of ruminants, such as cows and sheep, to break down the cellulose that they eat. In this process the cellulose is made via fermentation by cellulolytic fungi such as *Trichoderma reesei* and *Trichoderma viride*. The enzymatic method is typically carried out in four or five stages. The cellulose is pretreated to make the raw material, such as wood or straw, more amenable to hydrolysis. Next the cellulase enzymes are used to break the cellulose molecules into fermentable sugars. Following hydrolysis, the sugars are separated from residual materials and added to the yeast. The hydrolyzate sugars are fermented to ethanol using yeast. Finally, the ethanol is recovered by distillation. Alternatively, the hydrolysis and fermentation can be carried out together by using special bacteria or fungi that accomplish both processes. When both steps are carried out together the process is called sequential hydrolysis and fermentation (SHF).

Hops acid in conjunction with organic acids can be introduced for microbiological efficacy at various points in the enzymatic method of hydrolysis. Hops acid in conjunction with organic acid can be used in the production, manufacture and fermentation of cellulase enzymes made by *Trichoderma* and other fungi strains. The hops acid and organic acid can be added in the cellulosic simultaneous saccharification and fermentation phase (SSF). The hops acid and organic acid can be introduced in the sequential hydrolysis and fermentation (SHF) phase. They could also be introduced at a point before, during or after the fermentation by cellulolytic fungi that create the cellulase enzymes. Alternatively the hops acid in conjunction with organic acid can be added during the yeast fermentation phase, as discussed above.

The gasification process does not break the cellulose chain into sugar molecules. First, the carbon in the cellulose is converted to carbon monoxide, carbon dioxide and hydrogen in a partial combustion reaction. Then, the carbon monoxide, carbon dioxide and hydrogen are fed into a special fermenter that uses a microorganism such as *Clostridium Ijungdahlii* that is capable of consuming the carbon monoxide, carbon dioxide and hydrogen to produce ethanol and water. Finally, the ethanol is separated from the water in a distillation step. Hops acid and organic acid can be used as an antimicrobial agent in the fermentation step involving microorganisms such as *Clostridium Ijungdahlii* that are capable of consuming carbon monoxide, carbon dioxide and hydrogen to produce ethanol and water.

In one non-limiting embodiment, hops acid and organic acid are added to a tank and diluted to a predetermined concentration at a predetermined ratio. In the tank, hops acid extract, such as isomerized alpha extract, and an organic acid, like citric acid, are dissolved in water to form a hops acid and organic acid blend. The concentration of the hops acid extract solution and the organic acid solution in the batch tank can vary across a wide range. The blended hops acid extract/organic acid solution is then exhausted from the batch tank through an outlet at a specified dosage rate to create a solution of the desired concentration.

In one non limiting embodiment the ratio of hops acid to organic acid is from 1:200 to 1:20 ratio. The tank is typically a pre-mix tank.

A process vessel containing an aqueous microorganism solution is fluidly connected to the batch tank via outlets on the batch tank. The process vessel could be a cook vessel, fermentation tank, conditioning tank, starter tank, propagation tank, liquefaction vessel and/or piping or heat exchanger between these units. The hops acid extract/organic acid solution into the process vessel is capable of promoting propagation of producing microorganism present while simultaneously decreasing the concentration of undesirable microorganisms.

For smaller scale production of fermentation products, skid-mounted equipment is ideal. Skid mounting allows the equipment to be manufactured off site, shipped to the desired location and easily installed. This ensures ease in transportation, faster erection and commissioning. The batch tank, process vessel and connecting equipment could be made in a skid-mounted fashion.

The hops acids and the organic acids can be combined and then added to the system to be treated. They may also be added sequentially or separately to the system to be treated. The ratio of hops acids to organic acids are added to the systems to be treated can be as high as from 1:6000 to 1:5, or 1:6000 to 1:10, or 1:500 to 1:10, or 1:200 to 1:20, or 1:100 to 1:10, or 1:100 to 1:20.

The organic acid can be used in amounts of from 12500 ppm down to 100 ppm in the invention, from 6250 down to 100 ppm, or from 4000 down to 100 ppm, or from 4000 down to 200 ppm, or from 1000 down to 100 ppm, or from 1000 down to 200 ppm. Generally at least 100 ppm or at least 200 ppm or at least 300 ppm of organic acid is used. Hops acid could be used in amount of 0.5 ppm to 20 ppm, or from 0.5 ppm to 15 ppm, or from 2 to 15 ppm, or from 2 to 12 ppm, or from 3 to 12 ppm, or from 3 to 10 ppm. Generally the amount of hops acid used in the invention is at least 2 ppm or at least 3 ppm. Organic acids that can be used in the invention include Citric, Benzoic and Propionic acid and their salts. The components of the invention (hops acid and organic acid) can be added to the aqueous system separately or blended prior to addition. The organic acids can be added to the aqueous side systems with other additives such as, but not necessarily restricted to, surfactants, scale and corrosion control compounds, ionic or non-ionic polymers, pH control agents, and other additives used for altering or modifying the chemistry of the aqueous system.

A person of ordinary skill in the art using the teaching described herein can determine the concentration of the composition required to achieve acceptable microbial control, and that the concentration is dependent on the matrix.

When used in a fermentation system the acids can be added in various locations in the fermentation system such as can be added in single or multiple locations in the fermentation process, including the slurry tank(s), cookers, mash coolers, propagators and fermentation tanks. One skilled in the art may also determine other addition points.

While particular elements, embodiments and applications of the present invention have been shown and described, it will be understood, of course, that the invention is not limited thereto since modifications can be made by those skilled in the art without departing from the scope of the present disclosure, particularly in light of the foregoing teachings.

EXAMPLES

The synergy indices reported in the following examples use the following formula, which was first reported in F. C. Kull, P. C. Eisman, H. D. Sylwestrowka, and R. L. Mayer, Applied Microbiology 9:538-541, 1961:

$$\text{Synergy Index} = Qa/QA + Qb/QB$$

where $Qa$ is the concentration of Antimicrobial A required to achieve complete inhibition of growth of the test microbe when used in combination with Antimicrobial B;

$QA$ is the concentration of Antimicrobial A required to achieve complete inhibition of growth of the test microbe when used alone;

$Qb$ is the concentration of Antimicrobial B required to achieve complete inhibition of growth of the test microbe when used in combination with Antimicrobial A;

$QB$ is the concentration of Antimicrobial B required to achieve complete inhibition of growth of the test microbe when used alone.

A synergy index (SI) of 1 indicates the interactions between the two antimicrobials is merely additive, a SI of greater than one indicates the two antimicrobials are antagonistic with each other, and a SI of less than 1 indicates the two antimicrobials interact in a synergistic manner.

In the following examples the endpoint used to measure levels of antimicrobial activity is known as the Minimal Inhibitory Concentration, or MIC. This is the lowest concentration of a substance or substances which can achieve complete inhibition of growth.

In order to determine the Minimal Inhibitory Concentration, a two-fold dilution series of the antimicrobial is constructed with the dilutions being made in growth media. The dilutions are made in a 96 well microplate such that each well has a final volume of 280 µl of media and antimicrobial. The first well has, for example, a concentration of 1000 µM antimicrobial, the second 500 µM, the third 250 µM, and so forth, with the $12^{th}$ and final well in the row having no antimicrobial at all and serving as a positive growth control. After the dilution series is constructed the wells receive an inoculum of microbe suspended in growth media such that the final concentration of microbes in the well is ~5×10 cfu/ml. In these examples the test microbe used is *Lactobacillus plantarum*. The cultures are incubated at 37° C. for 18-24 hours, and the wells scored as positive or negative for growth based on a visual examination for turbid wells, with turbidity being an indicator of growth. The lowest concentration of antimicrobial which completely inhibits growth (eg., a clear well) is designated the Minimal Inhibitory Concentration.

In order to determine whether the interaction between two antimicrobials is additive, antagonistic, or synergistic against a target microbe a modification of the MIC method known as the "checkerboard" method is employed using 96 well microplates. To construct a checkerboard plate the first antimicrobial is deployed using the two-fold serial dilution method used to construct an MIC plate, except that each of the eight rows is an identical dilution series which terminates after the eighth column. The second antimicrobial is deployed by adding identical volumes of a twofold dilution series at right angles to the first series. The result is each well of the 8×8 well square has a different combination of antimicrobial concentrations, yielding 64 different combinations in total. The $9^{th}$ and $10^{th}$ columns receive no antimicrobial at all and serve as positive and negative growth controls, respectively. After the checkerboard microplate is constructed, it is inoculated with *Lactobacillus plantarum*, incubated at 37° C., and scored as described for the MIC method.

Example 1

Synergy of Citric Acid with Hops Acids

Minimal inhibitory concentrations were determined for both citric acid and hops acid at pH 6 using the protocol described above with *Lactobacillus plantarum* as the test microbe. Checkerboard synergy plates were constructed as described, the wells inoculated to a final concentration of ~5×10$^5$ cfu/ml, incubated for 18-24 hours, and then scored visually for growth/no growth. Synergy indices were calculated according to the formula described by Kull et al. This example demonstrates that the effect of combining citric acid and hops acid is greater than the effect of either antimicrobial alone. The amount of citric acid needed to inhibit bacterial growth is reduced from 100,000 ppm to 391-12,500 ppm. The concentration of hops acid drops from 31.3 ppm to a range of 1.96-15.6 ppm.

TABLE 1

| Used alone | | Used in Combination | | | |
|---|---|---|---|---|---|
| Citric Acid MIC (QA) ppm | Hops acid MIC (QB) ppm | Citric Acid MIC (Qa) ppm | Hops Acid MIC (Qb) ppm | Citric Acid: Hops Acid Ratio | Synergy index |
| 100000 | 31.3 | 12500 | 1.96 | 6378:1 | 0.188 |
| 100000 | 31.3 | 6250 | 3.91 | 1593.1 | 0.187 |
| 100000 | 31.3 | 3125 | 7.81 | 400:1 | 0.281 |
| 100000 | 31.3 | 1563 | 7.81 | 200:1 | 0.265 |
| 100000 | 31.3 | 781 | 15.6 | 50:1 | 0.506 |
| 100000 | 31.3 | 391 | 15.6 | 25:1 | 0.502 |

Example 2

Synergy of Benzoic Acid with Hops Acids

Minimal inhibitory concentrations were determined for both citric acid and hops acid at pH 6 using the protocol described above with *Lactobacillus plantarum* as the test microbe. Checkerboard synergy plates were constructed as described, the wells inoculated to a final concentration of ~5×10$^5$ cfu/ml, incubated for 18-24 hours, and then scored visually for growth/no growth. Synergy indices were calculated according to the formula described by Kull et al. This example demonstrates that the effect of combining citric acid and hops acid is greater than the effect of either antimicrobial alone. The amount of citric acid needed to inhibit bacterial growth is reduced from 100,000 ppm to 391-12,500 ppm. The concentration of hops acid drops from 31.3 ppm to a range of 1.96-15.6 ppm.

TABLE 2

| Used alone | | Used in Combination | | | |
|---|---|---|---|---|---|
| Benzoic Acid MIC (QA) ppm | Hops acid MIC (QB) ppm | Benzoic Acid MIC (Qa) ppm | Hops Acid MIC (Qb) ppm | Benzoic Acid:Hops Acid Ratio | Synergy Index |
| 100000 | 31.3 | 50000 | 1.96 | 25510:1 | 0.563 |
| 100000 | 31.3 | 25000 | 1.96 | 12755:1 | 0.313 |

Example 3

Fermentation Lab Data

Evaluations were conducted at the National Corn-to-Ethanol Research Center, utilizing hops acid extracts and citric acid. The samples tested and their concentrations can be found in FIG. 1 and Table 3. The tests were conducted to evaluate the effects of ternary antimicrobials on ethanol production in corn mash produced under conditions that are similar to those used in the fuel ethanol industry. Two specific effects were investigated: (1) the ability of antimicrobials to affect ethanol yield and sugar conversion in fermentations that are contaminated by lactic acid bacteria, and (2) the ability of antimicrobials to control bacterial infections compared to control bacteria-free fermentations. Three 160-gram slurries of corn flour, water and enzyme (30% w/w dry solids) were made for each treatment and control (inoculated and uninoculated). The slurries were incubated for 90 minutes at 83° C., cooled to 40° C., and then inoculated with *L. plantarum*. Next, the slurries were dosed with antimicrobial. The facility dosed chlorine dioxide, hops acid extracts and citric acid to 250-mL Erlenmeyer flasks and samples were collected at 15, 30 and 60 minutes post antimicrobial addition. After the 3 time-point samples were collected, the pH of the mash was adjusted to <5.2 by addition of 300 µl of 5-N sulfuric acid. All enzymes, nutrients, and other amendments added to the fermentation flasks were freshly prepared before use. Urea was added as a sterile 0.2-g/ml solution to a final concentration of 500 ppm (w/w) based on the nitrogen content of the urea (w/w, based on the total mass of mash). The glucoamylase enzyme (Spirizyme Excel, Novozymes) was prepared as a 0.25-g/ml solution and added at a dose of 0.066% (w/w, based on the wet weight of corn). Sterile water was added to equalize the total solids content of each treatment. All fermentation flasks were inoculated with a 0.2-g/ml suspension of yeast (*Saccharomyces cerevisiae*). This suspension was incubated and mixed for 30 minutes at 40° C. before inoculation into the fermentation flasks. Each fermentation flask was Inoculated with 170 µl of the yeast suspension to attain an initial concentration of 1×10$^7$ yeast cells/ml. The mass of each flask was recorded after all additions were made, then sanitized fermentation traps were inserted into each flask and they were weighed again. The flasks were incubated at 32° C. with shaking at 170 rpm in an incubator/shaker for a total of 64 hours. Fermentation progress was monitored by weighing the fermentation flasks periodically during the 3-day incubation (at 0, 17.5, 22.5, 42.5, 48, and 64 hrs after inoculation with yeast). The concentrations of substrates (glucose, DP2, DP3, and DP4+, where "DPx" represent glucose oligomers with "x" subunits) and products (ethanol, glycerol, lactic acid, and acetic acid) were measured by HPLC at the end of fermentation. Samples were prepared for HPLC by centrifugation to remove large solids, followed by filtration through 0.45-µm syringe filters, and acidification to pH of approximately 2 by addition of sulfuric acid to a final concentration of 0.01 N. The final pH, concentrations of total dry solids and dissolved dry solids, and the density of the beer filtrate was measured were measured after incubation for 64 hours. Samples from each flask were plated for bacterial colony counts.

TABLE 3

| Time (hours) | Control (×10$^5$ cfu) | 5 Hops/ 200 Citric (×10$^6$ cfu) | 5 Hops/ 400 Citric (×10$^5$ cfu) | 10 Hops/ 400 Citric (×10$^6$ cfu) |
|---|---|---|---|---|
| 0.25 | 1.30 | 1.30 | 1.01 | 0.745 |
| 0.5 | 0.9 | 1.14 | 1.19 | 0.535 |
| 1 | 3.47 | 10.7 | 5.28 | 3.19 |
| 64 | 0.0334 | 0.00424 | 0.00208 | 0.0000167 |

This example shows that during fermentation, 5 ppm of hops acids combined with 200 ppm of citric acid is effective in reducing bacteria, which was unexpectedly low after seeing the laboratory MIC and synergy data. Combining 5 ppm hops acids with 400 ppm citric acid gave even better results The synergistic mixture of 10 ppm hops acid/400 ppm citric acid gave approximately a 3 log reduction (99.9% reduction) in *Lactobacillus*.

Figure 2:
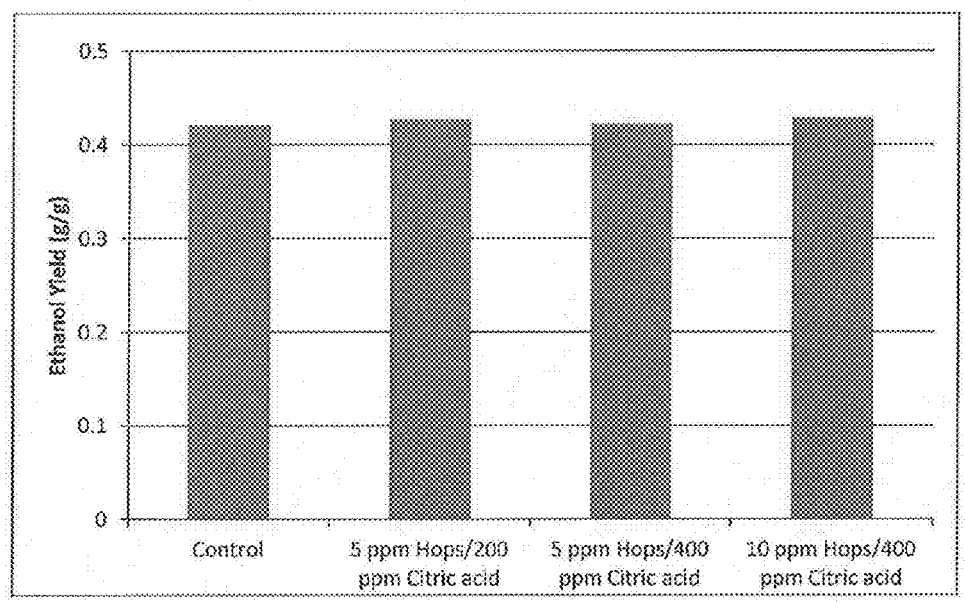
FIG. 2 is a graph depicting the average ethanol yield for treatments expressed as grams ethanol per grams of dry corn.

FIG. 2 and Table 4 show the average ethanol yields of the uninfected control and the three samples after fermentation. No significant differences were observed in the average ethanol yields among all treatments (P=0.055), using ANOVA. In FIG. 2 and table 4 the data represent the average of three independent replicate fermentation flasks

TABLE 4

| Hops/citric add dosage | Ethanol Yield |
|---|---|
| Infection free control | 0.421 |
| 5 ppm Hops/200 ppm Citric add | 0.427 |
| 5 ppm Hops/400 ppm Citric add | 0.422 |
| 10 ppm Hops/400 ppm Citric add | 0.429 |

Average ethanol yield for treatments expressed as grams ethanol per grams of dry corn.

What is claimed is:

1. A method of controlling undesirable microorganism concentration in an aqueous solution employed in a fermentation process, the method comprising the steps of:
    (a) introducing a fermentable carbohydrate to an aqueous solution;
    (b) introducing at least one yeast to said solution;
    (c) introducing a hops acid extract into said solution; and
    (d) introducing an organic acid into said solution;
wherein the organic acid is selected from the group consisting of citric acid, benzoic acid, propionic acid and their salts.

2. The method of claim 1 wherein said steps are performed sequentially.

3. The method of claim 1 wherein the organic acid is citric acid.

4. The method of claim 1 wherein the amount of hops acid extract in the aqueous solution comprises from 2 ppm to 15 ppm.

5. The method of claim 1 wherein the hops acid extract has a dosage rate of at least 5 ppm.

6. The method of claim 1 wherein the organic acid has a dosage rate of at least 200 ppm.

7. The method of claim 1 wherein the organic acid has a dosage rate of at least 200 ppm and up to about 1000 ppm.

8. The method of claim 1 wherein the organic acid is citric acid or its salt and the ratio of hops acid extract to citric acid (or its salt) is from 1:25 to 1:6378.

9. The method of claim 1 wherein the organic acid is benzoic acid or its salt and the ratio of hops acid extract to benzoic acid (or its salt) is 1:12,755 to 1:25,510.

10. The method of claim 1 wherein the organic acid is propionic acid or its salt and the ratio of hops acid extract to propionic acid (or its salt) is 1:12,000 to 1:10000.

11. A method of controlling undesirable microorganism concentration in an aqueous fluid solution employed in a fermentation process, the method comprising the steps of:
    (a) introducing a fermentable carbohydrate to an aqueous system;
    (b) introducing at least one desirable microorganism which is capable of fermenting carbohydrate to said aqueous system;
    (c) introducing at least one hops acid extract into said aqueous system; and
    (d) introducing at least one organic acid into said aqueous system;
wherein the organic acid is selected from the group consisting of citric acid, benzoic acid, propionic acid and their salts.

12. The method of claim 11 wherein the organic acid is citric acid.

13. The method of claim 11 wherein the hops acid extract has a dosage rate in the aqueous system of at least 2 ppm to 15 ppm.

14. The method of claim 11 wherein the hops acid extract has a dosage rate in the aqueous system of at least 5 ppm to about 10 ppm.

15. The method of claim 11 wherein the organic acid has a dosage rate of least 200 ppm in the aqueous system.

16. The method of claim 11 wherein the desirable microorganism is selected from the group consisting of a yeast, a fungi, a bacteria or combination thereof.

17. A method of reducing residual byproduct of antibiotic in a fermentation process, the method comprising the steps of:
    (a) introducing a fermentable carbohydrate to an aqueous system;
    (b) introducing at least one yeast to said system;
    (c) introducing a hops acid extract into said system; and
    (d) introducing an organic acid into said system;
wherein the organic acid is selected from the group consisting of citric acid, benzoic acid, propionic acid and their salts.

* * * * *